United States Patent [19]
Mitra et al.

[11] Patent Number: 5,890,486
[45] Date of Patent: Apr. 6, 1999

[54] THERMAL NASAL DILATOR AND METHOD OF TREATMENT FOR RELIEF OF NASAL CONGESTION AND OTHER SYMPTOMS ASSOCIATED WITH COMMON COLD AND ALLERGIES

[75] Inventors: Sekhar Mitra, Guangzhou, China; Brian Joseph McCormick, Loveland, Ohio; Kishor Jivanlal Desai, West Chester, Ohio; Jeffrey Alan Darner, Hamilton, Ohio; Michael James Simone, Wyoming, Ohio

[73] Assignee: The Procter & Gamble Company, Cincinnati, Ohio

[21] Appl. No.: 108,681

[22] Filed: Jul. 1, 1998

Related U.S. Application Data

[63] Continuation-in-part of Ser. No. 955,877, Oct. 22, 1997, which is a continuation of Ser. No. 771,192, Dec. 20, 1996, abandoned.

[51] Int. Cl.$^6$ .............................. A61F 5/08; A61M 15/00; A61M 16/00; A62B 7/00
[52] U.S. Cl. .............................. 128/200.24; 128/204.13; 606/199; 606/204.45
[58] Field of Search .......................... 128/200.24, 204.13, 128/204.12, 207.18, 848, DIG. 26; 606/199, 204.45; 602/74, 41, 47, 54–59, 902

[56] References Cited

U.S. PATENT DOCUMENTS

| | | | |
|---|---|---|---|
| Re. 35,408 | 12/1996 | Petruson | 128/858 |
| 4,201,217 | 5/1980 | Slater | 128/342 |
| 4,414,977 | 11/1983 | Rezakhany | 128/342 |
| 5,046,479 | 9/1991 | Usui | 126/204 |
| 5,342,412 | 8/1994 | Ueki | 607/114 |
| 5,366,492 | 11/1994 | Ueki | 607/114 |
| 5,476,091 | 12/1995 | Johnson | 128/200.24 |
| 5,479,944 | 1/1996 | Petruson | 128/858 |
| 5,533,499 | 7/1996 | Johnson | 128/200.24 |
| 5,533,503 | 7/1996 | Doubek et al. | 128/200.24 |
| 5,546,929 | 8/1996 | Muchin | 128/200.24 |
| 5,549,103 | 8/1996 | Johnson | 128/200.24 |
| 5,553,605 | 9/1996 | Muchin | 128/200.24 |
| 5,706,800 | 1/1998 | Cronk | 128/200.24 |

FOREIGN PATENT DOCUMENTS

| | | | |
|---|---|---|---|
| HEI 7-49042 | 5/1995 | Japan | A61F 7/08 |
| 2126-101-A | 3/1984 | United Kingdom | A62B 9/06 |
| WO 88/03788 | 2/1988 | WIPO | A61F 5/56 |
| WO 8803-788-A | 2/1988 | WIPO | A61F 5/56 |
| WO 94/23675 | 10/1994 | WIPO | A61F 5/56 |

*Primary Examiner*—Kimberly L. Asher
*Attorney, Agent, or Firm*—Loy M. White; Douglas C. Mohl; T. David Reed

[57] ABSTRACT

The present invention relates to a nasal dilator which comprises a means for dilating the nostrils and a thermal element, which can be worn on the nose of a human for an extended period of time, as well as a method of treatment for relief of nasal congestion/blockage, sinus discomfort and pain, and other cold and/or allergy symptoms associated therewith, by applying said nasal dilator to the nose of a human in need of such treatment.

31 Claims, 10 Drawing Sheets

THERMAL NASAL DILATOR AND METHOD OF TREATMENT FOR RELIEF OF NASAL CONGESTION AND OTHER SYMPTOMS ASSOCIATED WITH COMMON COLD AND ALLERGIES

CROSS REFERENCE TO RELATED APPLICATION

This application is continuation-in-part of application Ser. No. 08/955,877, filed Oct. 22, 1997, which is a continuation of application Ser. No. 08/771,192, filed Dec. 20, 1996, abandoned.

TECHNICAL FIELD

The present invention relates to a nasal dilator which comprises a means for dilating the nostrils and at least one thermal element, which can be worn on the nose of a human for an extended period of time. The present invention also relates to a method of treatment for relief of nasal blockage, sinus discomfort and pain, and other cold symptoms associated therewith, as well as related symptoms associated with allergies, by applying said nasal dilator to the nose of a human in need of such treatment.

BACKGROUND OF THE INVENTION

Blockage of the nasal passages is obviously an inconvenience to persons who experience it. Blockage of the nasal passages is particularly uncomfortable at night, since it can lead to sleep disturbances, sleep irregularities, and/or snoring. In addition, a person with such a condition may wake often because he/she is not inhaling sufficient quantities of oxygen.

While there is a small portion of the human population which has some type of malformation of the nasal passages, such as a deviated septum, the majority of people who experience blockage of the nasal passages usually are suffering from the nasal congestion and other symptoms associated with the common cold and/or allergies. The common cold, although not usually a serious illness, is a highly prevalent, discomforting and annoying affliction. The term "common cold" is applied to minor respiratory illnesses caused by a variety of different respiratory viruses, of which rhinoviruses are the major known cause of common colds, accounting for approximately 50 percent of the colds in adults.

With the common cold, symptoms of nasal discharge, nasal congestion/blockage, and sneezing usually commence on the first day of illness and progress to maximum severity by the second or third day. Other symptoms may include mild burning of the eyes, loss of smell and taste, a feeling of pressure or fullness in the sinuses, sinus pain, headache, and vocal impairment. Many of these symptoms are shared by sufferers of allergies.

At present, treatment for the nasal congestion/blockage, sinus discomfort and pain, and other cold symptoms, including fever and the general malaise associated therewith, generally contain an analgesic (aspirin or acetaminophen) and one or more antihistamines, decongestants, cough suppressants, antitussives and expectorants; the majority of these drugs are taken orally. Other specific pharmaceutical actives for nasal symptoms (e.g., congestion) generally contain either oxymetazoline or phenylephrine and are generally delivered topically to the nasal mucosa via a nasal spray.

Nasal delivery of therapeutic agents has been well known for a number of years. See, for example, U.S. Pat. No. 4,749,700 to Wenig, issued Jun. 7, 1988, U.S. Pat. No. 4,778,810 to Wenig, et al., issued Oct. 18, 1988 and U.S. Pat. No. 4,729,997 to Wenig issued Mar. 8, 1988. Nasal saline sprays have been used to moisturize nasal passages and to dissolve build-up in the nasal mucosa; however, saline solutions alone have not proved satisfactory for relief of nasal congestion. Menthol has been administered orally from lozenges and the like, as well as delivered to the nasal mucosa from an inhaler, see for example, Clinical Otolaryngology, 1988, vol. 13, pp. 25–29. Yet menthol delivered in such a manner has not been found to provide a sufficient level of relief.

Another method of relieving the sinus pain, and other cold symptoms described above, is by application of heat to the nose and/or sinus areas. Such heat treatments include the use of hot towels and reusable thermal packs containing water and/or microwaveable gels. In general, such devices, which require the thermal source to be replenished, are inconvenient to use. Further, many of these thermal units or devices do not provide long lasting heat or maintain a consistent temperature over long periods of time. The beneficial therapeutic effects from this administration of heat diminishes after the heat source is removed; therefore, it is desirable to provide a sustained heat source to the afflicted area for as long as possible, preferably for about eight hours. These devices are also inconvenient to use at night, when the treatment is most often needed. Further, these thermal devices do little to aide breathing through the nose due to nasal congestion/blockage.

Nasal dilators for aiding breathing through the nose are known, however, these devices are also not generally effective in relieving nasal congestion/blockage, sinus discomfort and pain, and other cold/allergy symptoms. U.S. Pat. No. 4,414,977, issued to Rezakhany, discloses one such nasal dilator. The nasal dilator includes generally elongated top and bottom rings which are spaced apart and connected together by a rear strut and a front strut. The front strut is longer than the rear strut and includes a bend therein formed at a position close to the front end of the bottom ring. When in place in the nasal passage, the top ring fits in the nasal valve within the nostril to prevent the tissue from being drawn in during inhalation, and to reduce extra flow resistance during exhalation. The bottom ring fits above the entrance to the nostril and serves to stabilize the position of the top ring within the nasal passage. One of these nasal dilators must be inserted into each nasal passage to provide unobstructed breathing. These nasal dilators, however, are not always effective since they are uncomfortable to wear, may cause irritation and itching of the nostril, unsafe to use at night during sleep, and are inconvenient to use when the wearer has nasal drainage due to a cold.

Another nasal dilator is disclosed in U.S. Pat. No. 1,292,083, issued to Sawyer. This nasal dilator includes pads of adhesive material to which are attached metal loops. The pads are applied to the exterior surface of the nose above the nostrils. Once the pads are affixed, a dilating member is connected with each of the loops. The dilating member consists of a metal wire that provides a spring force which is directed outward or upward when hooked ends of the dilating member are engaged with the loops of the pads. A further nasal dilator is disclosed in U.S. Pat. No. 1,950,839, issued to Chirila. This nasal dilator is similar to that of Sawyer but employs suction cups to secure a dilating member to the exterior surface of the nose. These dilators are not always effective because the dilating members can easily become disengaged from the pads or suction cups that secure the dilating members to the exterior of the nose, which could cause injury to the face or eyes, particularly during sleep.

Other nasal dilators are disclosed in U.S. Pat. No. 5,533, 499, issued to Johnson, U.S. Pat. No. 5,533,503, issued to Doubek, et al., and U.S. Pat. No. 5,546,929, issued to Muchin. These nasal dilators comprise a truss comprising a flexible strip and spring member which traverses the bridge of the nose. The flexible strip adheres to the exterior surface of the nose such that the ends of the truss member stabilize the outer wall of the nostrils, thereby preventing the outer wall from drawing in during breathing.

While the above described nasal dilators may aid breathing through the nose in a healthy person, it is evident that there is a continuing need for an improved means of treating the nasal congestion/blockage, sinus discomfort and pain, and other cold/allergy symptoms associated therewith. For example, Cronk, et al. have disclosed in U.S. Pat. No. 5,706,800, a nasal dilator which includes an aromatic medication or transdermal medication disposed on the dilator. Unfortunately, these devices are not completely effective, and therefore, a need for a nasal dilator that can provide safe and effective relief of these symptoms still exists. Moreover, there still is a need for a nasal dilator that can be reliably worn at night when the nasal congestion/blockage problem is most acute and most uncomfortable. In addition, there still is a need for a nasal dilator that can be reliably worn through extended therapeutic periods without discomfort to the wearer. The nasal dilator should also be of efficient design and relatively uncomplicated.

The inventors of the present invention have developed a nasal dilator which comprises a means for dilating congested and/or blocked nasal passages due to the common cold and/or allergies and at least one thermal element to relieve the sinus discomfort and pain, and other cold/allergy symptoms associated therewith, which can be safely and comfortably worn, day or night, on the nose of a human for an extended period of time. The present inventors have also discovered a method of treatment for relief of the nasal congestion/blockage, sinus discomfort and pain, and other cold/allergy symptoms associated therewith, by applying said nasal dilator to the nose of a human in need of such treatment.

It is therefore an object of the present invention to provide a nasal dilator which comprises a means for dilating the nostrils and at least one thermal element which can be safely and comfortably worn, day or night, on the nose of a human for an extended period of time.

It is also an object of the present invention to provide a method of treatment for relief of the nasal congestion/blockage, sinus discomfort and pain, and other cold symptoms associated therewith, by applying said nasal dilator to the nose of a human in need of such treatment.

It is a further object of the present invention to provide a method of treatment for relief of the nasal congestion/blockage, sinus discomfort and pain, sneezing, and other symptoms associated with allergies, by applying said nasal dilator to the nose of a human in need of such treatment.

These objectives and additional objectives will become readily apparent from the detailed description which follows.

SUMMARY OF THE INVENTION

The present invention comprises a nasal dilator which comprises a unitary truss member having an elongated shape and a normally, substantially planar state. The truss member comprises a strip of flexible base material having a first side and a second side, a first end region adapted to engage the outer nasal tissue of a first nasal passage and a second end region adapted to engage the outer nasal tissue of a second nasal passage, coupled to one another by an intermediate segment configured to traverse the bridge of the nose of a human. The truss member is held in place on the nose of a human by a layer of an adhesive substance, which extends over the first and second end regions, and preferably the intermediate segment, of the first side of the flexible base material. The truss member acts to draw the outer nasal tissues of the first and second nasal passages outward, by way of a resilient means, preferably comprising at least one resilient member, which extends along, and substantially parallel to, the longitudinal extent of the unitary truss member. The truss member also comprises at least one thermal element capable of providing heat or cold, preferably the thermal element provides heat and comprises an exothermic composition comprising iron oxidation chemistry. The truss member still further comprises a strip of flexible top material having a first side and a second side. The peripheral edges of first side of the strip of flexible top material are bonded to the peripheral edges of the second side of the flexible base material to seal the at least one thermal element, and preferably the resilient means, between the flexible top and base materials. At least one of the flexible top and base materials may be oxygen-permeable or made oxygen-permeable, such that when the truss member is removed from its air-impermeable secondary package, the exothermic composition is activated and begins to generate controlled and sustained heat. The nasal dilator of the present invention may also comprise an aromatic and/or pharmaceutical therapeutic component.

The present invention also comprises a method of treatment to open the nasal passages blocked by congestion and/or swelling associated with the common cold and/or allergies and encourage free breathing. Such a treatment relieves the symptoms of nasal discharge, nasal congestion/blockage, and sneezing, as well as other symptoms which may include mild burning of the eyes, loss of smell and taste, a feeling of pressure or fullness in the sinuses, sinus pain, headache, and vocal impairment by applying said truss member to the nose of a human in need of such treatment.

BRIEF DESCRIPTION OF THE DRAWINGS

While the specification concludes with claims which particularly point out and distinctly claim the present invention, it is believed that the present invention will be better understood from the following drawings, taken in conjunction with the accompanying description of preferred embodiments, in which like reference numerals identify identical elements and wherein:

FIG. 1a–1d are multiple perspective views of a portion of a face with a nasal dilator in accordance with the present invention secured to a nose wherein:

FIG. 1a is a perspective view of a portion of a face with a nasal dilator, as substantially described in FIGS. 2 and 5, secured to a nose;

FIG. 1b is a perspective view of a portion of a face with a nasal dilator, as substantially described in FIG. 3, secured to a nose;

FIG. 1c is a perspective view of a portion of a face with a nasal dilator, as substantially described in FIGS. 4, 6, and 7, secured to a nose; and FIG. 1d is a perspective view of a face showing a nasal dilator comprising a resilient means, traversing the bridge of the user's nose, for drawing the outer wall tissue of the nasal passages outward, two separate compartments of particulate exothermic composition positioned near the middle of the unitary truss member and directly over the nasal passages of the user to apply heat to the nasal passages, and two separate compartments of particulate exothermic composition positioned toward the ends of the unitary truss member to apply heat to the front of the face below the eyes of the user, including but not limited to the maxillary sinuses.

FIGS. 8a–8c are multiple sectional views of a portion of a face showing the nose wherein:

FIG. 8a is a sectional view of a portion of a face showing a nose and nasal passages in a normal state of breathing;

FIG. 8b is a sectional view of a portion of a face showing a nose and nasal passages in a state of swelling and/or congestion; and FIG. 8c is a sectional view of a portion of a face showing a nose and nasal passages with a nasal dilator, as described in FIGS. 1–7, secured to a nose.

DETAILED DESCRIPTION OF THE INVENTION

Figure 1A:
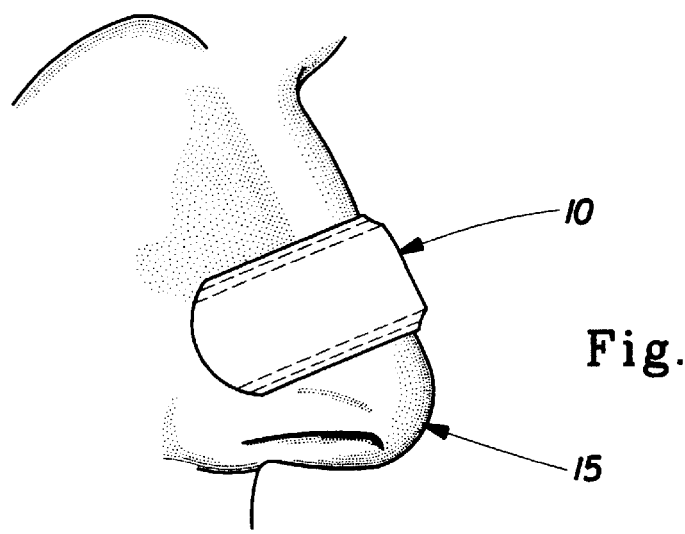
Figure 1B:
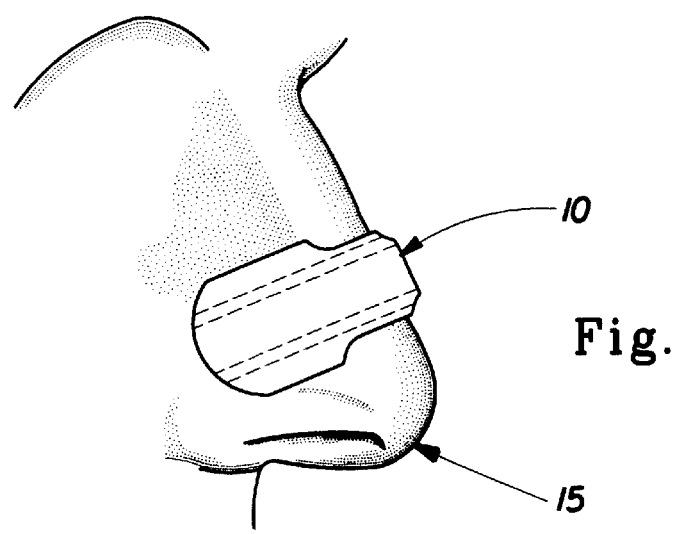
Figure 1C:
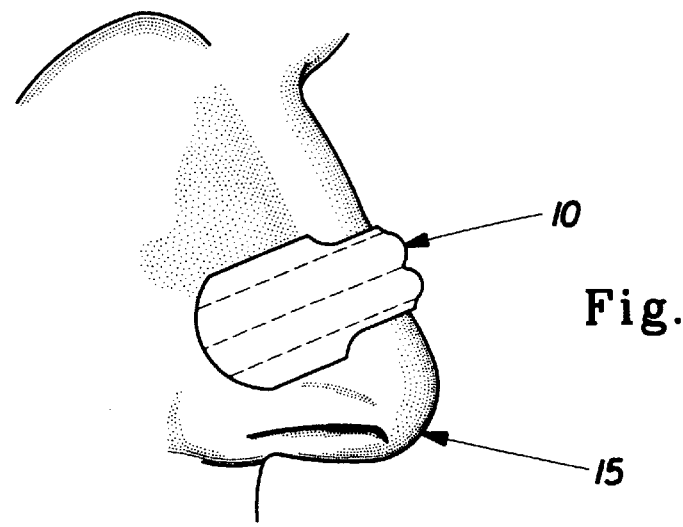
Figure 1D:
Figure 2:
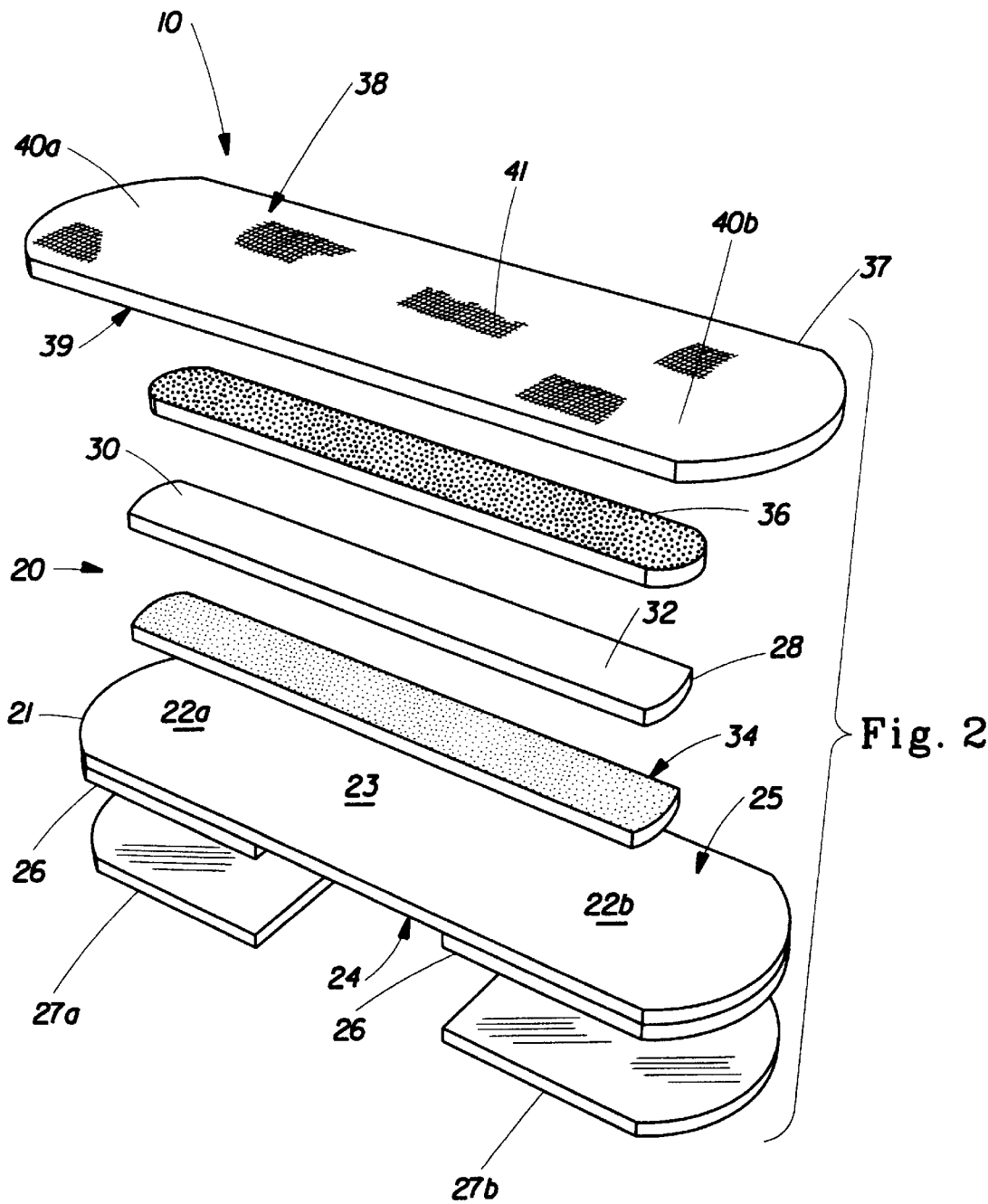
FIG. 2 is an exploded perspective view showing the components of one embodiment of the nasal dilator in accordance with the present invention which comprises a single resilient member and wherein the intermediate segment of the truss is the same width as the width of the first and second ends of the truss.
Figure 3:
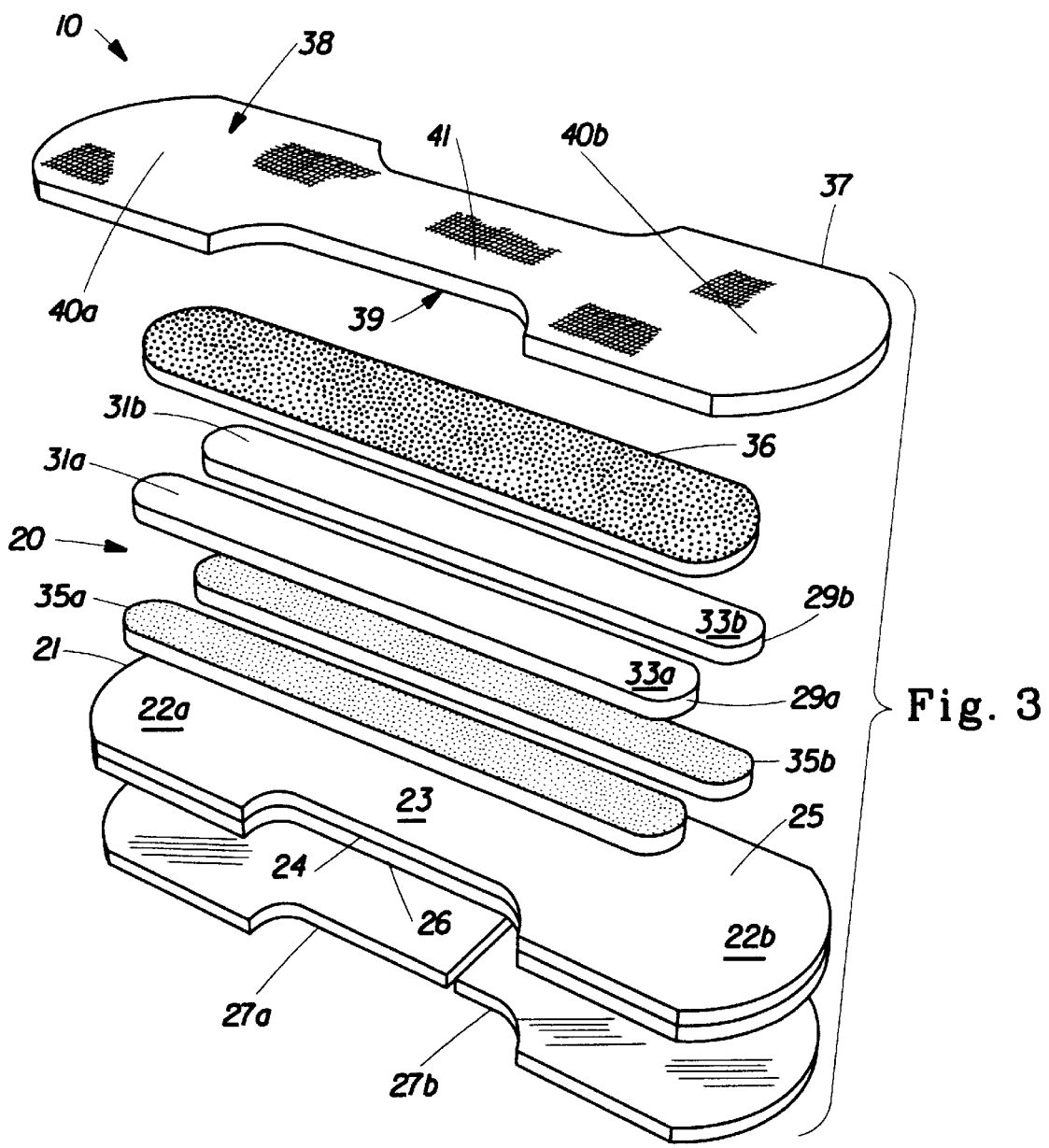
FIG. 3 is an exploded perspective view showing the components of one embodiment of the nasal dilator in accordance with the present invention which comprises two resilient members and wherein the intermediate segment of the truss has a width less than the width of the first and second ends of the truss.
Figure 4:
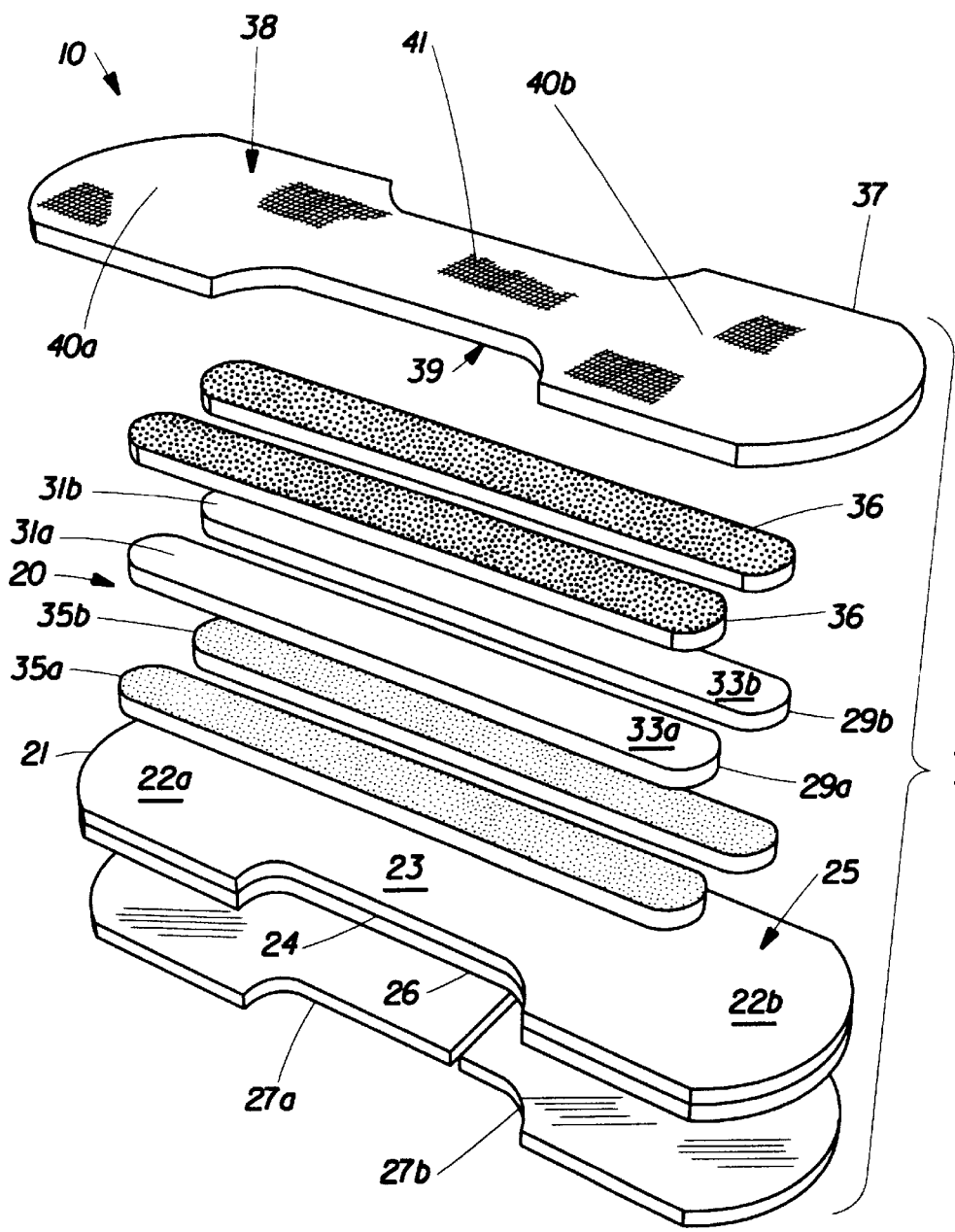
FIG. 4 is an exploded perspective view showing the components of another embodiment of the nasal dilator in accordance with the present invention which comprises two resilient members and two separate compartments of particulate exothermic composition.
Figure 5:
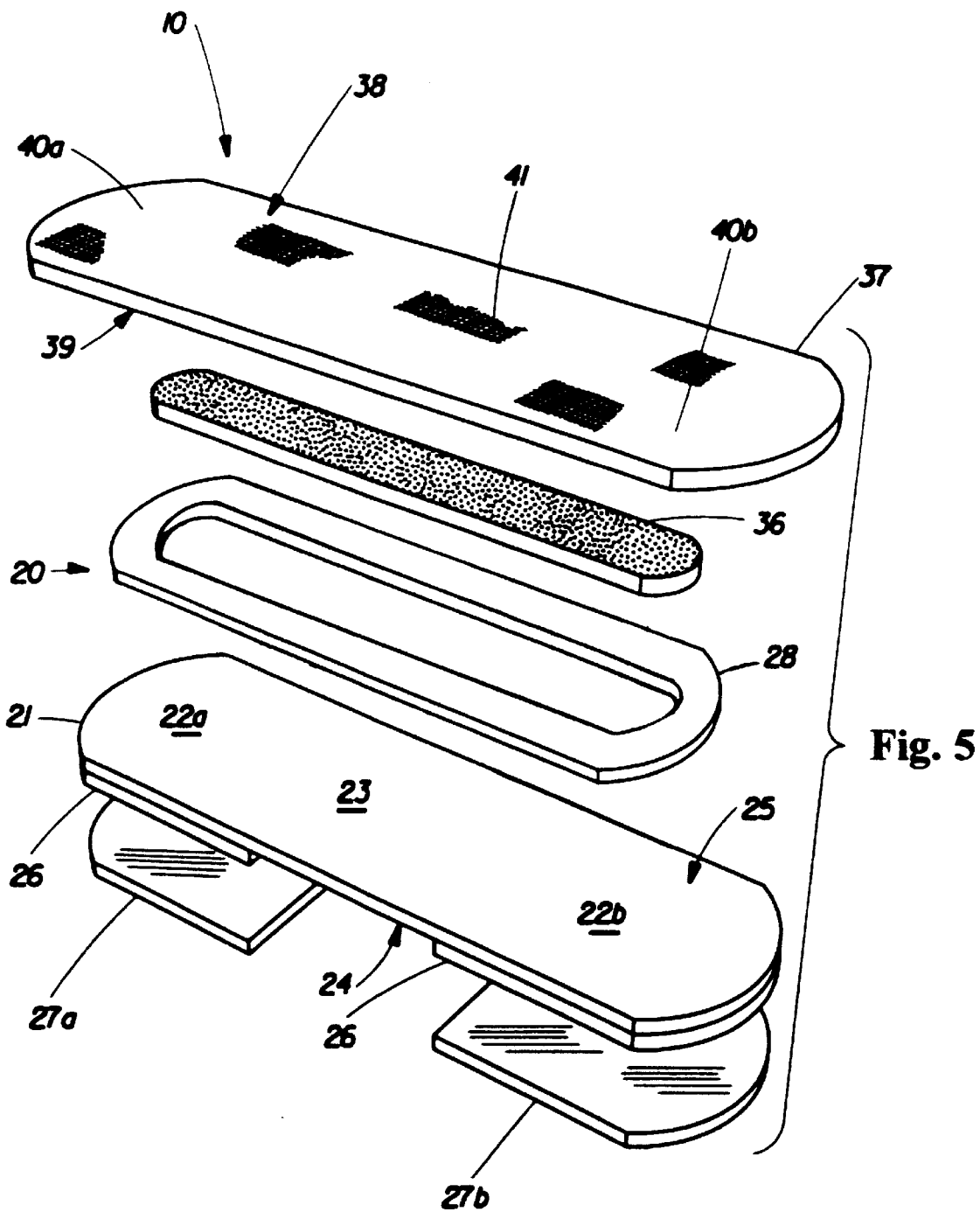
FIG. 5 is an exploded perspective view showing the components of another embodiment of the nasal dilator in accordance with the present invention which comprises a single, substantially racetrack shaped, resilient member and wherein the particulate exothermic composition resides substantially within the center of resilient member.
Figure 6:
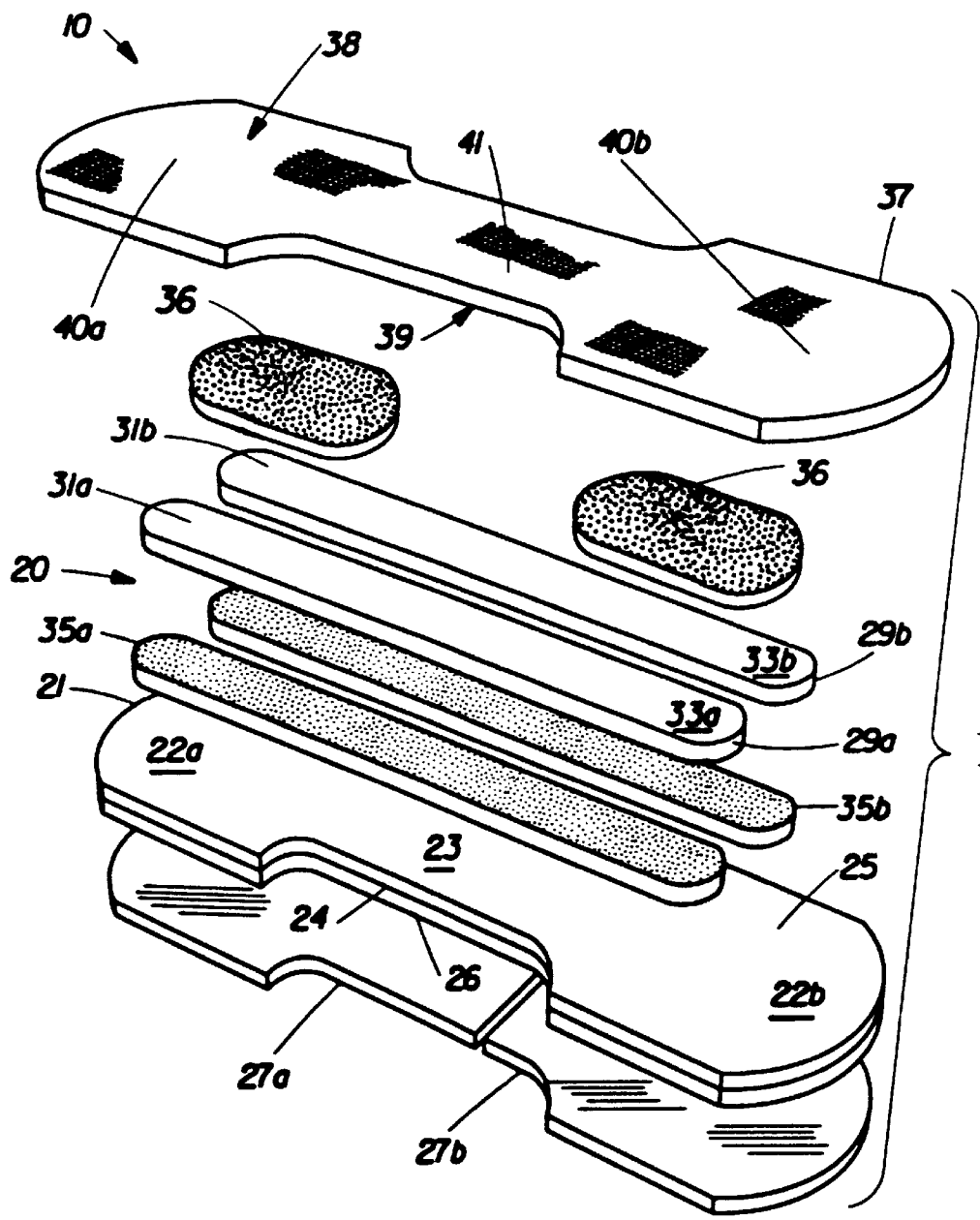
FIG. 6 is an exploded perspective view showing the components of another embodiment of the nasal dilator in accordance with the present invention which comprises two resilient members and two separate compartments of particulate exothermic composition which are preferably positioned directly over the nasal passages of the user.

A nasal dilator 10 in accordance with the present invention is illustrated generally in FIGS. 1a, 1b, 1c, and 1d. The nasal dilator 10 is shown secured to the nose 15 of a human.

The nasal dilator 10, shown in FIGS. 2–7 comprises a unitary truss member 20, having an elongated shape and a normally, substantially planar state, and which comprises a strip of flexible base material 21 having a first end region 22a, adapted to engage a first outer wall tissue 43 of a first nasal passage 45, and a second end region 22b, adapted to engage a second outer wall tissue 44 of a second nasal passage 46, coupled by an intermediate segment 23, configured to traverse the bridge of the nose 15 of a human. While the intermediate segment 23 may be the same width as the width of the first and second end regions 22a and 22b, the preferred width of the intermediate segment 23 is less than the width of the first and second end regions 22a and 22b. The strip of flexible base material 21 also comprises a first side 24 and a second side 25. The strip of flexible base material 21 may be made of any suitable material. However, the preferred materials for the strip of flexible base material 21 are film layer laminates. The first side 24 of the strip of flexible base material 21 is typically made of nonwoven fabric, to provide support, laminated to the second side 25 of the strip of flexible base material 21 which is preferably a film having heat sealability and capable of being easily thermally fused. The second side 25 may also be a liquefied silicone rubber coating applied to the non-woven fabric of the first side 24. For the non-woven fabrics of the first side 24, those having preferred characteristic properties of light weight and high tensile strength, including but not limited to, nylon, rayon, cellulose ester, polyvinyl derivatives, polyolefins, polyamides, or polyesters, cuproammonium cellulose (Bemberg) and other high molecular weight compounds, as well as natural materials such as, wool, silk, jute, hemp, cotton, linen, sisal, or ramie, are suitable. These nonwoven materials are generally described in Riedel "Nonwoven Bonding Methods and Materials", *Nonwoven Worlds* (1987), incorporated herein by reference in its entirety. Examples of the film of the second side 25, include but are not limited to, polyethylene, polypropylene, nylon, polyester, polyvinyl chloride, polyvinylidene chloride, polyurethane, polystyrene, saponified ethylene-vinyl acetate copolymer, ethylene-vinyl acetate copolymer, natural rubber, reclaimed rubber and synthetic rubber. These materials may also be coextruded with low melt temperature polymers. The strip of flexible base material 21 thickness is in the range of about 1 to about 300 $\mu$m and may be oxygen permeable or impermeable. A preferred strip of flexible base material 21 of the present invention comprises a first side 24 of a polypropylene nonwoven sheet laminated to a second side 25 film of low-density polyethylene (LDPE), having a thickness of about 5 to about 100 $\mu$m. A more preferred second side 25 film comprises a coextruded film having a first side of polypropylene and a second side of a low melt temperature copolymer, such as EVA.

Web material composed of continuous filaments of thermoplastic resin laminated with a thermoplastic resin film, such as those described in Japanese Kokai Patent Application No. HEI 07-067907, published Mar. 14, 1995, incorporated herein by reference in its entirety, may also be useful in the present invention.

The strip of flexible base material 21 also comprises on its first side 24, a layer of an adhesive substance 26 which extends over the first end region 22a and second end region 22b, preferably over the first end region 22a, second end region 22b, and the intermediate segment 23, of the strip of flexible base material 21. The adhesive substance 26 is preferably a breathable, acrylic, pressure sensitive, biocompatible adhesive. Readily removable, first and second release liners 27a and 27b, respectively, cover the adhesive substance 26 on the first end region, second end region, and intermediate segment 22a, 22b, and 23 on the first side 24 of the strip of flexible base material 21. The first release liner 27a and second release liner 27b cover the adhesive substance 26 and remain in place on the strip of flexible base material 21 until the nasal dilator 10 is used.

The unitary truss member 20 further comprises a resilient means extending along said unitary truss member 20 such that said resilient means is oriented substantially parallel to a longitudinal extent of said unitary truss member 20. The resilient means may comprise a single resilient member 28, or a first resilient member 29a and a second resilient member 29b. The resilient member(s) have a first end 30, 31a, and 31b, and a second end 32, 33a, and 33b, respectively. The resilient member(s) 28, 29a, and 29b typically terminate at the end edges of the first and second end regions 22a and 22b of the strip of flexible base material 21 and/or first end region 40a and second end region 40b of strip of flexible top material 37. However, the resilient member(s) 28, 29a, and 29b may terminate anywhere within the first and second end regions 22a and 22b of the strip of flexible base material 21 and/or first end region 40a and second end region 40b of strip of flexible top material 37. The resilient member(s) 28, 29a, and 29b may be made from any suitable material having the appropriate axial and torsional flexibility, such as metal and/or plastic. The preferred material for the resilient members 28, 29a, and 29b is an industrial grade, biaxially oriented polyester that is approximately 2 mm to 8 mm wide and 0.25 mm thick, and may optionally have a plurality of grooves that extend substantially parallel to the respective resilient members 28, 29a, and 29b. The grooves create areas of reduced material to enhance the flexibility of the resilient members 28, 29a, and 29b in a direction perpendicular to the plurality of grooves.

The resilient members 28, 29a, and 29b are preferably secured to the second side 25 of the flexible base material 21 by one or more strips of flexible adhesive material 34, 35a, and 35b. The strips of flexible adhesive material 34, 35a, and 35b are of the same amount, size, and shape as the resilient members 28, 29a, and 29b, respectively. Each strip of flexible adhesive material 34, 35a, and 35b is preferably a double-sided adhesive, foam tape or an acrylic, pressure sensitive bio-compatible adhesive material, such as 3M-1509, available from Minnesota, Mining, & Manufacturing, Inc., St. Paul, Minn.

The unitary truss member 20 further comprises a strip of flexible top material 37 having a first side 38, a second side 39, a first end region 40a, a second end region 40b, and an intermediate segment 41. The first end region 40a, second end region 40b, and intermediate segment 41 are of the same size and shape as the first end region 22a, second end region 22b, and intermediate segment 23, respectively, of the strip of flexible base material 21. The strip of flexible top material 37 may be made of any suitable material. However, the preferred materials for the strip of flexible top material 37 is generally the same as for the strip of flexible base material 21, that is, film layer substrates wherein the first side 38 is a nonwoven fabric, to provide support, laminated to the second side 39 which is a film having heat sealability and capable of being easily thermally fused. The strip of flexible top material 37 thickness is in the range of about 1 to about 300 $\mu$m and may be oxygen permeable or impermeable. The preferred film layer substrates for the strip of flexible top material 37 comprise a first side 38 of polypropylene nonwoven sheets laminated to a second side 39 of a film of poly(ethylene-vinyl acetate), having a thickness of about 5 to about 100 $\mu$m. A more preferred second side 39 film comprises a coextruded film having a first side of polypropylene and a second side of a low melt temperature copolymer, such as EVA.

Figure 7:
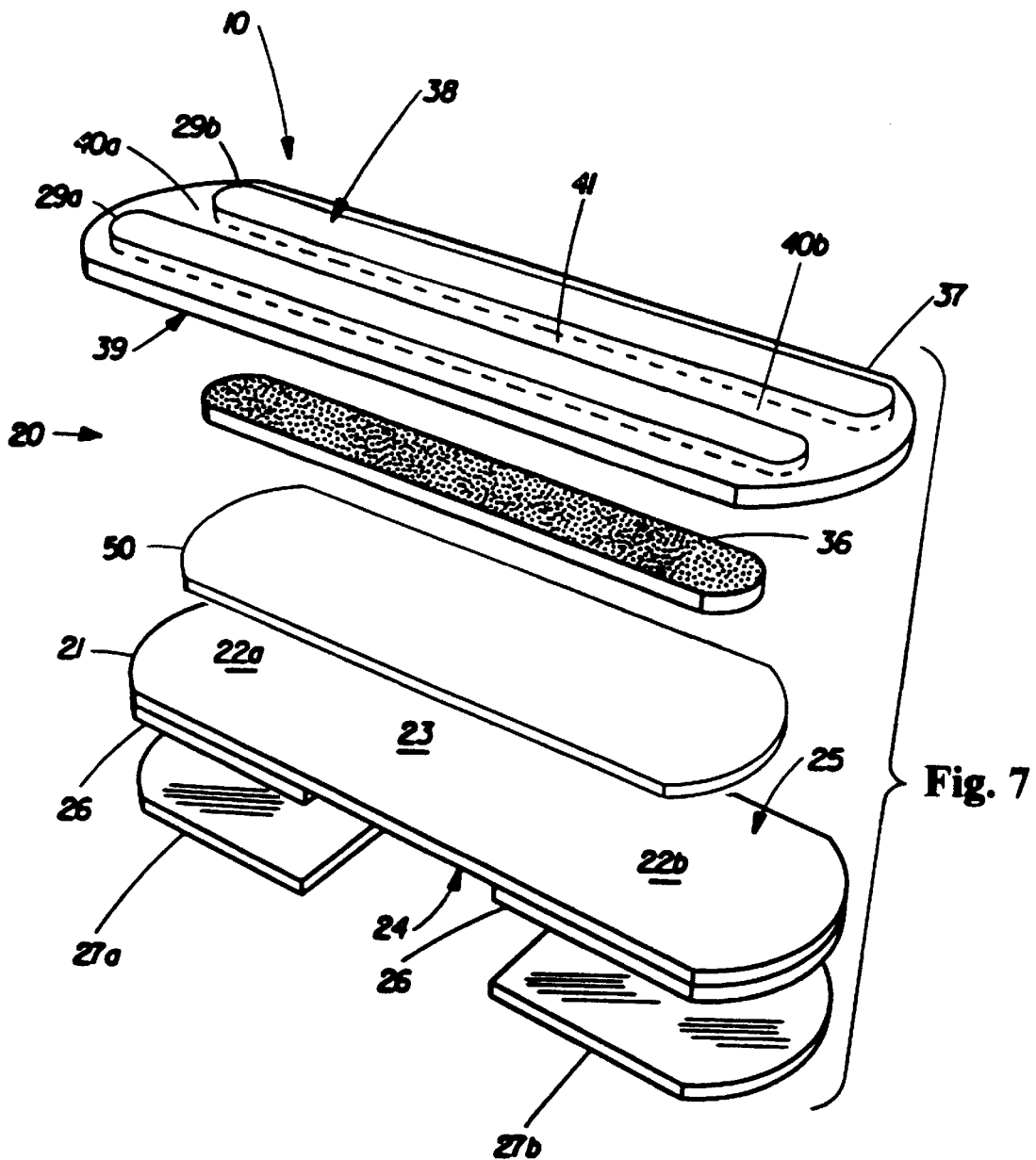
FIG. 7 is an exploded perspective view showing the components of another embodiment of the nasal dilator in accordance with the present invention which comprises a strip of flexible top material wherein the resilient means is extruded within the flexible top material and an aromatic/pharmaceutical component.

The strip of flexible top material 37 may alternatively be extruded such that resilient members 28 or 29a and 29b, are formed within the preferred film layer substrate for the strip of flexible top material 37, as typically shown in FIG. 7. In a further alternative, the strip of flexible base material 21 may be extruded such that resilient members 28 or 29a and 29b, are formed within the preferred film layer substrate for the strip of flexible base material 21.

The unitary truss member 20 further comprises at least one thermal element 36. The thermal element 36 preferably extends from the first end region 22a to second end region 22b along the unitary truss member 20 substantially parallel to a longitudinal extent of said unitary truss member 20, and preferably terminates at the edge of the first and second end regions 22a and 22b of the strip of flexible base material 21 and/or the edge of the first and second end regions 40a and 40b of the strip of flexible top material 37. In the alternative, the at least one thermal element 36 may terminate anywhere within the first and second end regions 22a and 22b of the strip of flexible base material 21 and/or the first and second end regions 40a and 40b of the strip of flexible top material 37. In the further alternative, the at least one thermal element 36 may terminate within the first and second end regions 22a and 22b of the strip of flexible base material 21 and/or the first and second end regions 40a and 40b of the strip of flexible top material 37, such that thermal element 36 does not traverse intermediate segment 23. That is, the at least one thermal element 36 are located such that they reside substantially over first and second nasal passages 44 and 45, and not over the bridge of the nose 15. This embodiment may further comprise additional thermal elements 36 which extend over the cheeks of the user to apply heat to the front of the user's face below the eyes, including but not limited to the maxillary sinuses.

Most any thermal composition, such as exothermic compositions, microwaveable compositions, heat of crystallization compositions, and the like, as well as compositions capable of producing a cooling effect, may be used for thermal element 36 in the present invention. However, the preferred thermal element of the present invention is thermogenic and comprises a particulate exothermic composition. While the particulate exothermic composition may comprise any composition capable of generating heat, the particulate exothermic composition preferably comprises, but is not limited to, powdered iron, powdered carbon, metal salt, and water. Compositions of this type react when exposed to oxygen providing heat for several hours. In the alternative, the unitary truss member 20 may comprise a composition capable of producing a cooling effect.

The particulate exothermic composition typically comprises from about 30% to about 80% iron powder, from about 3% to about 25% activated carbon, non-activated carbon, and mixtures thereof, from about 0.5% to about 10% of a metal salt, and from about 1% to about 40% water.

Suitable sources for iron powder include cast iron powder, reduced iron powder, electrolytic iron powder, scrap iron powder, pig iron, wrought iron, various steels, iron alloys, and the like and treated varieties of these iron powders. There is no particular limitation to their purity, kind, etc. so long as it can be used to produce heat-generation with electrically conducting water and air.

Active carbon prepared from coconut shell, wood, charcoal, coal, bone coal, etc. is useful, but those prepared from other raw materials such as animal products, natural gas, fats, oils and resins are also useful in the present invention. There is no limitation to the kinds of active carbon used, however, the preferred active carbon has superior water holding capabilities. The capabilities of the carbon can be extended by using mixtures of the above carbons, i.e., active and non-activated carbon powders blended to reduce cost. Therefore, mixtures of the above carbons are useful in the present invention as well.

Useful metal salts include sulfates such as ferric sulfate, potassium sulfate, sodium sulfate, manganese sulfate, magnesium sulfate; and chlorides such as cupric chloride, potassium chloride, sodium chloride, calcium chloride, manganese chloride, magnesium chloride and cuprous chloride. Also, carbonate salts, acetate salts, nitrates, nitrites and other salts can be used. Among these metal salts, the deliquescent salts such as calcium chloride, magnesium chloride, etc. are very hygroscopic and hence these compounds, even when added in a small amount, show an effectiveness in inhibiting the escape of water vapor. Sodium chloride shows small solubility difference vs. temperature difference and hence no crystal is precipitated at low temperatures, and also provides reasonable heat-generation. Thus, deviation of heat-generation due to temperature difference of atmospheric air does not occur. In general, several suitable alkali, alkaline earth, and transition metal salts exist which can also be used, alone or in combination, to sustain the corrosive reaction of iron. The preferred metal salts of the present invention are sodium chloride, cupric chloride, and mixtures thereof.

The water used herein may be from any appropriate source. There is no particular limitation to its purity, kind, etc.

While oxygen is necessary for the oxidation reaction of iron to occur, an internal oxygen source is not required in the present invention, however, oxygen-producing chemical materials may be incorporated in the particulate exothermic composition at the time of preparation thereof without changing the scope of the present invention. The oxygen sources used for the purpose of this invention include air and artificially made oxygen of various purity. Among these oxygen sources, air is preferred since it is the most convenient and inexpensive.

In addition to the above described components of the particulate exothermic compositions of the present invention, other components may also be added as appropriate, such as additional water-holding materials including vermiculite, porous silicates, wood powder, wood flour, cotton cloth having a large amount of fluffs, short fibers of cotton, paper scrap, vegetable/grain matter, super absorbent water-swellable or water-soluble polymers and resins, carboxymethylcellulose salts, and other porous materials having a large capillary function and hydrophilic properties; agglomeration aids including gelatin, natural gums, cellulose derivatives, cellulose ethers and their derivatives, starch, modified starches, polyvinyl alcohols, polyvinylpyrrolidone, sodium alginates, polyols, glycols, glycerin, corn syrup, sucrose syrup, sorbitol syrup and other polysaccharides and their derivatives, polyacrylamides, polyvinyloxoazolidone, and maltitol syrup; dry binders including maltodextrin, sprayed lactose, co-crystallized sucrose and dextrin, modified dextrose, sorbitol, mannitol, glycerin, petroleum waxes, natural/synthetic citrates, microcrystalline cellulose, microfine cellulose, pre-gelatinized starch, dicalcium phosphate, and calcium carbonate; oxidation reaction enhancers including elemental chromium, manganese, or copper, compounds comprising said elements, or mixtures thereof; hydrogen gas inhibitors including inorganic or organic alkali compounds or alkali weak acid salts such as sodium hydroxide, potassium hydroxide, sodium hydrogen carbonate, sodium carbonate, calcium hydroxide, calcium carbonate, and sodium propionate; fillers including natural cellulosic fragments including wood dust, cotton linter, and cellulose, synthetic fibers in fragmentary form including polyester fibers, foamed synthetic resins such as foamed polystyrene and polyurethane, and inorganic compounds including silica powder, porous silica gel, sodium sulfate, barium sulfate, iron oxides, and alumina; and anti-caking agents including tricalcium phosphate and sodium silicoaluminate. Such components also include thickeners such as cornstarch, potato starch, carboxymethylcellulose, and α-starch, and surfactants such as those included within the anionic, cationic, nonionic, zwitterionic, and amphoteric types. Still other additional components which may be added to the particulate exothermic compositions of the present invention, as appropriate, include extending agents such as metasilicates, zirconium, and ceramics.

Preferably at least 50%, more preferably 70%, even more preferably 80% and most preferably 90% of all of the particles by weight of the particulate exothermic composition of the present invention have a mean particle size of less than 200 μm, preferably less than 150 μm.

The above-mentioned components of the composition may be blended while being isolated from air using conventional blending techniques. Suitable methods of blending these components are described in detail in U. S. Pat. No. 4,649,895 to Yasuki et al., issued Mar. 17, 1987 which is incorporated by reference herein. For example, carbon is added to a blender or mixer, followed by water and this combination is mixed. Usually enough water is added to assist in blending while avoiding escalated corrosion, e.g., 3.5% by weight of the particulate composition. Also, therapeutic agents may be added to the composition at this time. Mixing is stopped and, in the absence of air, vermiculite and sodium chloride are added together. Mixing is resumed until all the components are mixed thoroughly and iron powder is added and mixed. The composition is then blended until thoroughly mixed. Additional water is added to the particulate composition during construction of the nasal dilator of the present invention. The above method may be modified as required, such as the salt and additional water may be added to the particulate composition as brine during construction of the nasal dilator.

In the alternative, the dry powdered components of the present invention, except water, may be blended, using conventional blending techniques and agglomerated into granules. For example, powdered carbon and a metal salt are added to a blender or mixer, and blended into a uniform dry mixture. An additional water-holding material is added and the composition is mixed until uniform. For this particular method, dry binders may be optionally added to the composition along with the additional water-holding material. Powdered iron is added and the mixture is again blended until uniform. An agglomeration aid is then added to the blended powders. The composition is mixed until a light agglomeration is formed. The agglomerated granules useful in the exothermic compositions of the present invention are easily wetted, less dense particles and soft porous granules. The granules formed by the agglomeration process may be optionally "rounded" on a rotary granulator, and fines reattached prior to being placed into a nasal dilator of the present invention. While the above described method of making the exothermic composition is by dry agglomeration, wet agglomeration techniques may also be used.

Individual nasal dilators 10 of the present invention can typically be prepared by bonding the strip of flexible base material 21 to the strip of flexible top material 37 around their peripheral edges, such that the second side 25 of the strip of flexible base material 21 faces and is fused to the second side 39 of the strip of flexible top material 37. This forms a pouch, envelope, or pocket with the second side 25 of the strip of flexible base material 21 and the second side 39 of the strip of flexible top material 37 toward the inside of the pouch, envelope, or pocket and the first side 24 of the strip of flexible base material 21 and the first side 38 of the strip of flexible top material 37 toward the outside, thereby sealing the resilient members 28, 29a, and 29b, strips of flexible adhesive material 34, 35a, and 35b, and the particulate exothermic composition, inside the pouch, envelope, or pocket, and thereby forming a unified structure which forms the nasal dilator 10 of the present invention. Bonding of the strip of flexible base material 21 to the strip of flexible top material 37 around their peripheral edges is typically done using a low heat, however, other means, such as an adhesive or thermoforming, may also be used.

While it is preferred that thermal elements 36 are incorporated into unitary truss member 20 between the strip of flexible top material 37 and the strip of flexible base material 21, thermal elements 36 may be made separately from unitary truss member 20. That is, an additional layer of flexible material, preferably a film having heat sealability and capable of being easily thermally fused, may be sealingly bonded to the first side 38 of the strip of flexible top material 37 around their peripheral edges encapsulating the particulate exothermic composition between the additional later of flexible material and the strip of flexible top material 37 to form thermal element 36. The additional layer of flexible material may then be sealingly bonded to the second side 25 of strip of flexible base material 21 around their peripheral edges, preferably encapsulating resilient members 28, 29a, and 29b and strips of flexible adhesive material 34, 35a, and 35b between the additional later of flexible material and the strip of flexible base material 21. Thermal element 36 may also be made such that it can be releasably attached to unitary truss member 20 by user.

Oxygen permeability can be provided by selecting films or film coatings for the second side 25 of the strip of flexible base material 21 and the second side 39 of the strip of flexible top material 37 forming the pouches, envelopes, pockets, that have the specifically desired permeability properties. Oxygen permeability can also be provided in the present invention by perforating the strip of flexible top material 37 with aeration holes using, for example, at least one pin, preferably an array of from about 20 to about 60 pins, with, e.g., tapered points and diameters of from about 0.2 mm to about 2 mm, preferably from about 0.4 mm to about 0.9 mm. The pins are pressed through the first and second side 38 and 39 of the strip of flexible top material 37 to a depth of from about 2% to about 100%, preferably from about 20% to about 100%, and more preferably from about 50% to about 100% into the particulate exothermic composition 36. This hole configuration provides an oxygen diffusion into the particulate exothermic composition 36 during the oxidation reaction of from about 0.01 cc $O_2$/min./5 cm$^2$ to about 15.0 cc $O_2$/min./5 cm$^2$ (at 21° C., 1 ATM), preferably from about 0.9 cc $O_2$/min./5 cm$^2$ to about 1.1 cc $O_2$/min./5 cm$^2$ (at 21° C., 1 ATM). Although there is preferably provided aeration holes in the strip of flexible top material 37, it is also possible to provide aeration holes in the strip of flexible base material 21, and/or both.

The velocity, duration, and temperature of the thermogenic oxidation reaction of the particulate exothermic composition can be controlled as desired by changing the area of contact with air, more specifically, by changing the oxygen diffusion/permeability.

The nasal dilator 10 of the present invention may optionally comprise a therapeutic component and/or agent, preferably added as a separate substrate layer 50. The therapeutic substrate layer 50 may be added between the strip of flexible base material 21 and the strip of flexible top material 37, between the strip of flexible base material 21 and the layer of adhesive substance 26, incorporated into the strip of flexible top material 37 and/or the strip of flexible base material 21, or added to the particulate exothermic composition of thermal element 36. The therapeutic component/agent may comprise, but is not limited to, active aromatic compounds, non-active aromatic compounds, pharmaceutical actives or other therapeutic agents, and mixtures thereof. For example, such active aromatic compounds include, but are not limited to, menthol, camphor, eucalyptus, and mixtures thereof, such non-active aromatic compounds include, but are not limited to, benzaldehyde, citral, decanal, aldehyde, and mixtures thereof, and such pharmaceutical actives/therapeutic agents include, but are not limited to, decongestants, antitussive agents, antihistamines, antibiotics, vitamins, antiviral agents, analgesics, anti-inflammatory agents including non-steriodal anti-inflammatory agents, antipruritics, antipyretics, anesthetic agents, antifungals, antimicrobials, and mixtures thereof. A person skilled in the pharmaceutical art would be able to select an appropriate therapeutic agent based upon the specific ailment being treated. While the therapeutic component/agent may be delivered to the user by breathing, the therapeutic component/agent is preferably delivered through the skin of the nose 15.

The finished nasal dilator 10 is packaged, by enclosing the nasal dilator 10, in a secondary air-impermeable package to prevent the oxidation reaction from occurring until desired as described in the aforementioned U.S. Pat. No. 4,649,895, already incorporated herein by reference. The nasal dilator remains sealed inside the air-impermeable package until a user is ready to apply the nasal dilator 10 to said user's nose 15, whereby opening the air-impermeable package enables oxygen from ambient air to activate the heating element to generate controlled and sustained heating. Alternatively, air impermeable removable adhesive strips can be placed over the aeration holes in the strip of flexible top material 37 such that, when the strips are removed, air is allowed to enter the strip of flexible top material 37, thus activating the oxidation reaction of the iron powder.

Figure 8A:
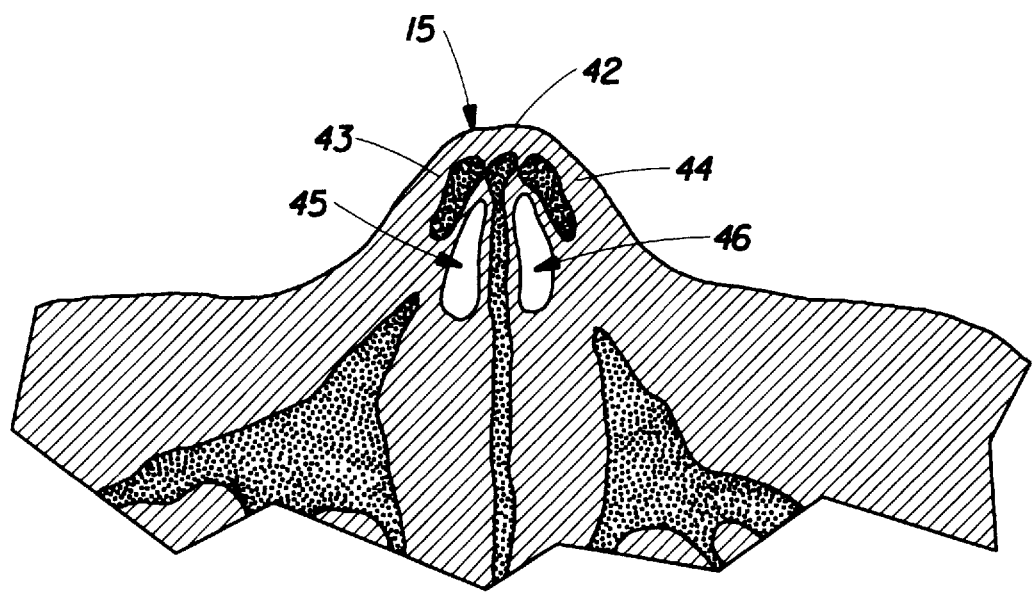
Figure 8B:
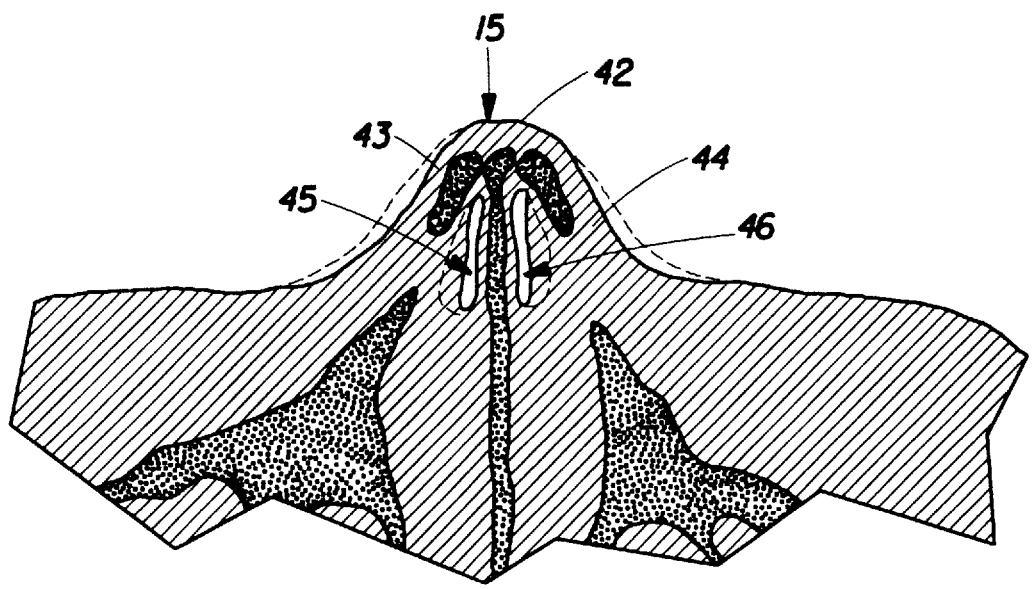
Figure 8C:
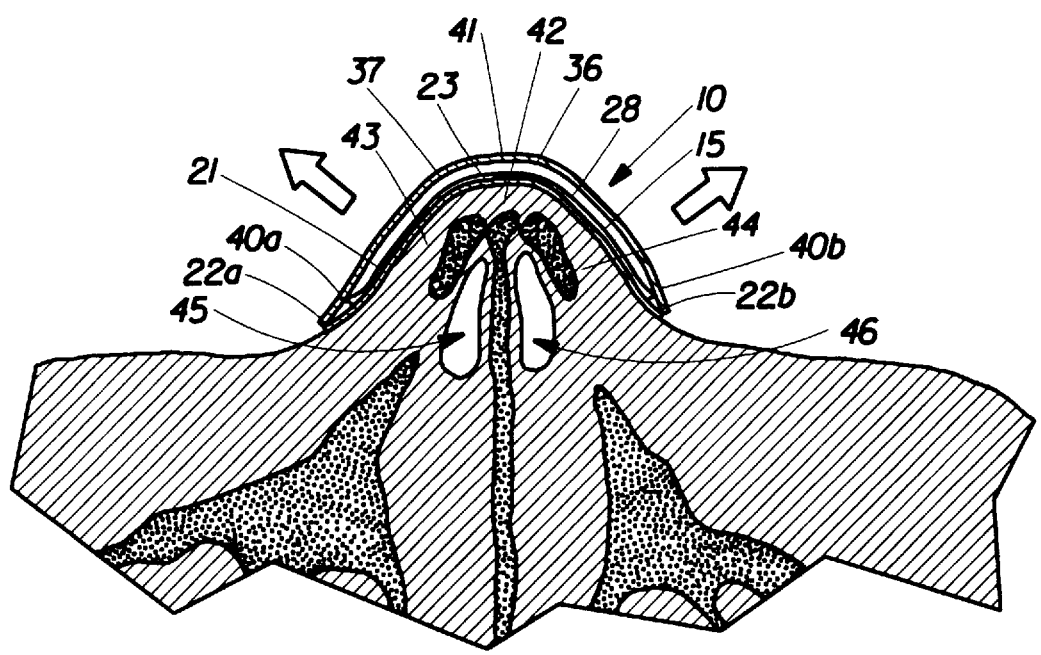

To secure the nasal dilator 10 to the nose 15, the first and second release liners 27a and 27b are removed from the strip of flexible base material 21 to expose the adhesive substance 26. As seen in FIGS. 1 and 8, the nasal dilator 10 is placed on the exterior of the nose 15 such that the nasal dilator 10 traverses the bridge of the nose 42 and the first and second end regions 22a and 22b of the strip of flexible base material 21 contact the first and second outer wall tissue 43 and 44 of the first and second nasal passages 45 and 46 of the nose 15. The adhesive substance 26 on the first and second end regions 22a and 22b and the intermediate segment 23 of the strip of flexible base material 21 releasably secures the unitary truss member 20 to the bridge of the nose 42 and to the first and second outer wall tissue 43 and 44 of the first and second nasal passages 45 and 46 of the nose 15.

With the nasal dilator 10 in place about the nose 15, the resiliency of the resilient members 28, 29a, and 29b act to stabilize the outer wall tissue 43 and 44 of the nose 15 and thereby draws the outer wall tissue 43 and 44 of the nose 15 outward. Moreover, the flexibility of the base material 21, strips of flexible adhesive material 34, 35a, and 35b and top material 37, the resiliency and flexibility of the resilient members 28, 29a, and 29b, all allow the nasal dilator 10 of the present invention to closely conform to the curves of the nose 15 of each individual wearer. The relative slight thickness of the material of the resilient members 28, 29a, and 29b, also enhances axial, torsional flexibility of the truss member 20 about the longitudinal extent of the truss member 20, which increases wearer comfort and facilitates adhesion of the adhesive substance 26 to the user's skin.

The desired functional range of dilating force (i.e., the spring biasing force due to the resiliency of the resilient members 28, 29a, and 29b, of the nasal dilator 10) is typically in the range of from about 5 grams to about 50 grams. Therefore, the nasal dilator 10 of the present invention is constructed to provide from about 5 grams to about 50 grams, preferably from about 10 grams to about 40 grams, and more preferably from about 20 to about 30 grams of dilating spring biasing force to each outer wall tissue 43 and 44 of the nasal passage 45 and 46 of the nose 15.

Nasal dilator 10 of the present invention can be comfortably worn through extended therapeutic periods. Moreover, nasal dilator 10 can be worn reliably at night when the inhalation nasal blockage problem is most acute, without anxiety and inconvenience normally associated with other nasal dilators. In addition, the nasal dilator 10 of the present invention is an efficient design that can be efficiently manufactured.

Although the present invention has been described and illustrated with reference to particular embodiments, those skilled in the art will recognize that various changes and modifications may be made in form and detail, such as those described in U.S. Pat. No. 5,533,499, issued to Johnson, U.S. Pat. No. 5,533,503, issued to Doubek, et al., and U.S. Pat. No. 5,546,929, issued to Muchin, all of which are incorporated, in their entirety herein by reference, without departing from the spirit and scope of the present invention, and it is intended to cover in the appended claims all such changes and modifications.

The nasal dilator 10 of the present invention may be applied to the nose 15 of a person suffering from symptoms of nasal discharge, nasal congestion/blockage, and sneezing, as well as other symptoms which may include mild burning of the eyes, loss of smell and taste, a feeling of pressure or fullness in the sinuses, sinus pain, headache, and vocal impairment usually associated with the common cold and/or allergies, for comfortable and convenient relief of said symptoms for an extended period of time.

What is claimed is:

1. A nasal dilator comprising a unitary truss member having an elongated shape and a normally, substantially planar state, comprising:
   a. a strip of flexible base material having a first side and a second side;
      a first end region adapted to fit over a first nasal passage;
      a second end region adapted to fit over a second nasal passage;
      an intermediate segment coupling said first end region to said second end region and configured to traverse a portion of a nose located between said first nasal passage and said second nasal passage; and
      a layer of an adhesive substance which extends over said first end region and said second end region of said first side of said strip of flexible base material to releasably engage said first end region with outer wall tissue of said first nasal passage and said second end region with outer wall tissue of said second nasal passage;
   b. a resilient means extending along said unitary truss member such that said resilient means is oriented substantially parallel to a longitudinal extent of said unitary truss member;
   c. at least one thermal element; and
   d. a strip of flexible top material having a first side and a second side wherein said second side of said strip of flexible top material is fixedly attached around its peripheral edges to the peripheral edges of said second side of said strip of flexible base material such that said at least one thermal element is sealed between said strip of flexible base material and said strip of flexible top material;
wherein the inherent tendency of said unitary truss member is to return to its normally planar state when flexed to engage said outer wall tissue of said first nasal passage and second nasal passage so as to pull said outer wall tissue of said first nasal passage and second nasal passage outward.

2. A nasal dilator according to claim 1 wherein said first side of said strip of flexible base material comprises a non-woven fabric laminated to said second side of said strip of flexible base material which comprises a film having heat sealability and capable of being thermally fused.

3. A nasal dilator according to claim 1 wherein said layer of an adhesive substance further extends over said intermediate segment of said first side of said strip of flexible base material.

4. A nasal dilator according to claim 2 wherein said strip of flexible base material comprises a film extruded to form said resilient means within said film.

5. A nasal dilator according to claim 1 wherein said resilient means comprises at least one resilient member fixedly attached to said second side of said strip of flexible base material, said resilient member having a first end which terminates within or at end edge of said first end region of said strip of flexible base material and a second end which terminates within or at end edge of said second end region of said strip of flexible base material, and said resilient member is sealed between said strip of flexible base material and said strip of flexible top material.

6. A nasal dilator according to claim 5 wherein said at least one resilient member comprises a substantially racetrack shape, wherein said at least one thermal element is inset within the center of said racetrack shaped resilient member.

7. A nasal dilator according to claim 1 wherein said at least one thermal element comprises a particulate exothermic composition for applying heat comprising:
   a.) from about 30% to about 80% iron powder;
   b.) from about 3% to about 25% activated carbon, non-activated carbon, and mixtures thereof;
   c.) from about 0.5% to about 10% metal salt; and
   d.) from about 1% to about 40% water.

8. A nasal dilator according to claim 7 wherein said exothermic composition further comprises components selected from the group consisting of additional water-holding materials, dry binders, agglomeration aids, and mixtures thereof.

9. A nasal dilator according to claim 7 further comprising an air-impermeable package enclosing said nasal dilator, wherein said nasal dilator remains sealed inside said air-impermeable package until a user is ready to apply said nasal dilator to said user's nose, whereby opening said air-impermeable package enables oxygen from ambient air to activate said heating element to generate controlled and sustained heating.

10. A method of treatment for relief of symptoms associated with the common cold comprising nasal discharge, nasal congestion and blockage, sneezing, mild burning of the eyes, loss of smell and taste, feeling of pressure or fullness in the sinuses, sinus pain, headache, and vocal impairment by applying said nasal dilator according to claim 7 to the nose of a person requiring such treatment.

11. A method of treatment for relief of symptoms associated with allergies comprising nasal discharge, nasal congestion and blockage, sneezing, mild burning of the eyes, loss of smell and taste, feeling of pressure or fullness in the sinuses, sinus pain, headache, and vocal impairment by applying said nasal dilator according to claim 7 to the nose of a person requiring such treatment.

12. A nasal dilator according to claim 1 wherein said at least one thermal element comprises a first end which terminates within or at end edge of said first end region of said strip of flexible base material and a second end which terminates within or at end edge of said second end region of said strip of flexible base material, and extends along said unitary truss member such that said at least one thermal element is oriented substantially parallel to said longitudinal extent of said unitary truss member.

13. A nasal dilator according to claim 12 wherein said at least one thermal element does not extend across said intermediate segment.

14. A nasal dilator according to claim 13 further comprising thermal elements which are adapted to extend over the cheeks of the user to apply heat to the front of the user's face below the user's eyes.

15. A method of treatment for relief of symptoms associated with the common cold comprising nasal discharge, nasal congestion and blockage, sneezing, mild burning of the eyes, loss of smell and taste, feeling of pressure or fullness in the sinuses, sinus pain, headache, and vocal impairment by applying said nasal dilator according to claim 14 to the nose of a person requiring such treatment.

16. A method of treatment for relief of symptoms associated with allergies comprising nasal discharge, nasal congestion and blockage, sneezing, mild burning of the eyes, loss of smell and taste, feeling of pressure or fullness in the sinuses, sinus pain, headache, and vocal impairment by applying said nasal dilator according to claim 14 to the nose of a person requiring such treatment.

17. A nasal dilator according to claim 1 wherein said first side of said strip of flexible top material comprises a non-woven fabric laminated to said second side of said strip of flexible top material which comprises a film having heat sealability and capable of being thermally fused.

18. A nasal dilator according to claim 17 wherein said strip of flexible top material comprises a film extruded to form said resilient means within said film.

19. A nasal dilator according to claim 1 wherein at least one of said strip of flexible base material and said strip of flexible top material are formed from an oxygen-impermeable film and are made oxygen-permeable by penetrating at least one of said strip of flexible base material and said strip of flexible top material with at least one pin to form at least one aeration hole.

20. A nasal dilator according to claim 19 wherein at least one of said strip of flexible base material and said second side of said strip of flexible top material are made oxygen-permeable by penetrating at least one of said strip of flexible base material and said strip of flexible top material with from about 20 to about 60 pins to form a plurality of aeration holes.

21. A nasal dilator according to claim 1 further comprising first and second release liners covering said layer of an adhesive substance, wherein said first and second release liners are readily removable from said strip of flexible base material to expose said adhesive substance and permit said unitary truss member to be releasably secured to said outer wall tissue of said first nasal passage and said second nasal passage.

22. A nasal dilator according to claim 21 wherein said first and second release liners further cover said said layer of an adhesive substance extending over said intermediate segment of said first side of said strip of flexible base material.

23. A nasal dilator according to claim 1 further comprising a therapeutic component which comprises a therapeutic agent selected from the group consisting of active aromatic compounds, non-active aromatic compounds, pharmaceutical actives or other therapeutic agents, and mixtures thereof.

24. A nasal dilator according to claim 23 wherein said therapeutic component comprises a separate substrate layer between said strip of flexible base material and said strip of flexible top material, a separate substrate layer between said strip of flexible base material and said layer of an adhesive substance, incorporated into said strip of flexible base material, incorporated into said strip of flexible top material, incorporated into said thermal element, or mixtures thereof.

25. A nasal dilator according to claim 24 wherein said therapeutic agent is delivered by breathing.

26. A nasal dilator according to claim 24 wherein said therapeutic agent is delivered through the skin of the nose and cheeks.

27. A nasal dilator according to claim 26 wherein said therapeutic agent is delivered through the skin of the nose.

28. A method of treatment for relief of symptoms associated with the common cold comprising nasal discharge, nasal congestion and blockage, sneezing, mild burning of the eyes, loss of smell and taste, feeling of pressure or fullness in the sinuses, sinus pain, headache, and vocal impairment by applying said nasal dilator according to claim 23 to the nose of a person requiring such treatment.

29. A method of treatment for relief of symptoms associated with allergies comprising nasal discharge, nasal congestion and blockage, sneezing, mild burning of the eyes, loss of smell and taste, feeling of pressure or fullness in the sinuses, sinus pain, headache, and vocal impairment by applying said nasal dilator according to claim 23 to the nose of a person requiring such treatment.

30. A method of treatment for relief of symptoms associated with the common cold comprising nasal discharge, nasal congestion and blockage, sneezing, mild burning of the eyes, loss of smell and taste, feeling of pressure or fullness in the sinuses, sinus pain, headache, and vocal impairment by applying said nasal dilator according to claim 1 to the nose of a person requiring such treatment.

31. A method of treatment for relief of symptoms associated with allergies comprising nasal discharge, nasal congestion and blockage, sneezing, mild burning of the eyes, loss of smell and taste, feeling of pressure or fullness in the sinuses, sinus pain, headache, and vocal impairment by applying said nasal dilator according to claim 1 to the nose of a person requiring such treatment.

* * * * *